United States Patent
Feinstein

(10) Patent No.: US 9,999,494 B2
(45) Date of Patent: *Jun. 19, 2018

(54) DEVICES, SYSTEMS, AND METHODS FOR REPAIR OF VASCULAR DEFECTS

(71) Applicant: Cook Medical Technologies LLC, Bloomington, IN (US)

(72) Inventor: Ara J. Feinstein, Paradise Valley, AZ (US)

(73) Assignee: Cook Medical Technologies LLC, Bloomington, IN (US)

(*) Notice: Subject to any disclaimer, the term of this patent is extended or adjusted under 35 U.S.C. 154(b) by 172 days.

This patent is subject to a terminal disclaimer.

(21) Appl. No.: 14/977,328

(22) Filed: Dec. 21, 2015

(65) Prior Publication Data

US 2016/0270899 A1    Sep. 22, 2016

Related U.S. Application Data

(63) Continuation of application No. 13/743,256, filed on Jan. 16, 2013, now abandoned, and a
(Continued)

(51) Int. Cl.
*A61F 2/07* (2013.01)
*A61M 27/00* (2006.01)
(Continued)

(52) U.S. Cl.
CPC ............. *A61F 2/07* (2013.01); *A61B 17/11* (2013.01); *A61B 17/12109* (2013.01);
(Continued)

(58) Field of Classification Search
CPC .. A61F 2/07; A61F 2/844; A61F 2/958; A61F 2/064; A61F 2/856; A61F 2/954; A61F 2230/0069; A61F 2210/0014; A61F 2250/0067; A61F 2250/0003; A61F 2002/075; A61B 17/11; A61B 17/12109;
(Continued)

(56) References Cited

U.S. PATENT DOCUMENTS 5,653,743 A * 8/1997 Martin ...................... A61F 2/07
606/153
6,071,307 A * 6/2000 Rhee ......................... A61F 2/07
623/1.13
(Continued)

*Primary Examiner* — Jocelin Tanner
(74) *Attorney, Agent, or Firm* — Brinks Gilson & Lione

(57) ABSTRACT

A balloon-expandable shunt is disclosed for shunting a vessel which has a graft with two ends and at least one expandable support element supporting the graft from within along a length at or near at least one of its ends. The shunt is bifurcated at an aperture that leads to a side-channel and which has a closed configuration and an open configuration such that when the aperture is in the closed configuration it defines a clot-resistant inner graft surface and when the aperture is in the open configuration it is configured to provide access to the shunt for a balloon that actuates the expandable support element. A balloon configured for actuating the shunt is also disclosed. A kit has a bifurcated graft with at least one expandable support element and a balloon for actuating the at least one expandable support element.

21 Claims, 8 Drawing Sheets

Related U.S. Application Data continuation-in-part of application No. 12/819,949, filed on Jun. 21, 2010, now Pat. No. 8,801,765, which is a continuation-in-part of application No. PCT/US2008/087849, filed on Dec. 19, 2008.

(60) Provisional application No. 61/587,570, filed on Jan. 17, 2012, provisional application No. 61/016,400, filed on Dec. 21, 2007, provisional application No. 61/055,428, filed on May 22, 2008.

(51) Int. Cl.
| | | |
|---|---|---|
| *A61F 2/06* | (2013.01) | |
| *A61B 17/11* | (2006.01) | |
| *A61B 17/12* | (2006.01) | |
| *A61F 2/958* | (2013.01) | |
| *A61F 2/844* | (2013.01) | |
| *A61M 39/02* | (2006.01) | |

(52) U.S. Cl.
CPC ........ *A61B 17/12136* (2013.01); *A61F 2/064* (2013.01); *A61F 2/844* (2013.01); *A61F 2/958* (2013.01); *A61M 27/002* (2013.01); *A61B 2017/111* (2013.01); *A61B 2017/1107* (2013.01); *A61B 2017/1132* (2013.01); *A61F 2002/075* (2013.01); *A61F 2210/0014* (2013.01); *A61F 2230/0069* (2013.01); *A61F 2250/0003* (2013.01); *A61F 2250/0067* (2013.01); *A61M 2039/0205* (2013.01)

(58) Field of Classification Search
CPC ...... A61B 17/12136; A61B 2017/1132; A61B 2017/1107; A61B 2017/111; A61B 2017/1139; A61B 2017/1135; A61M 27/002; A61M 2039/0205
See application file for complete search history.

(56) References Cited

U.S. PATENT DOCUMENTS

| | | | | |
|---|---|---|---|---|
| 6,440,166 | B1 * | 8/2002 | Kolluri | A61F 2/06 623/1.4 |
| 6,517,571 | B1 * | 2/2003 | Brauker | A61F 2/06 623/1.13 |
| 6,645,242 | B1 * | 11/2003 | Quinn | A61F 2/07 623/1.13 |
| 8,801,765 | B2 * | 8/2014 | Feinstein | A61B 17/11 623/1.11 |
| 2002/0038142 | A1 * | 3/2002 | Khosravi | A61F 2/07 623/1.13 |

* cited by examiner

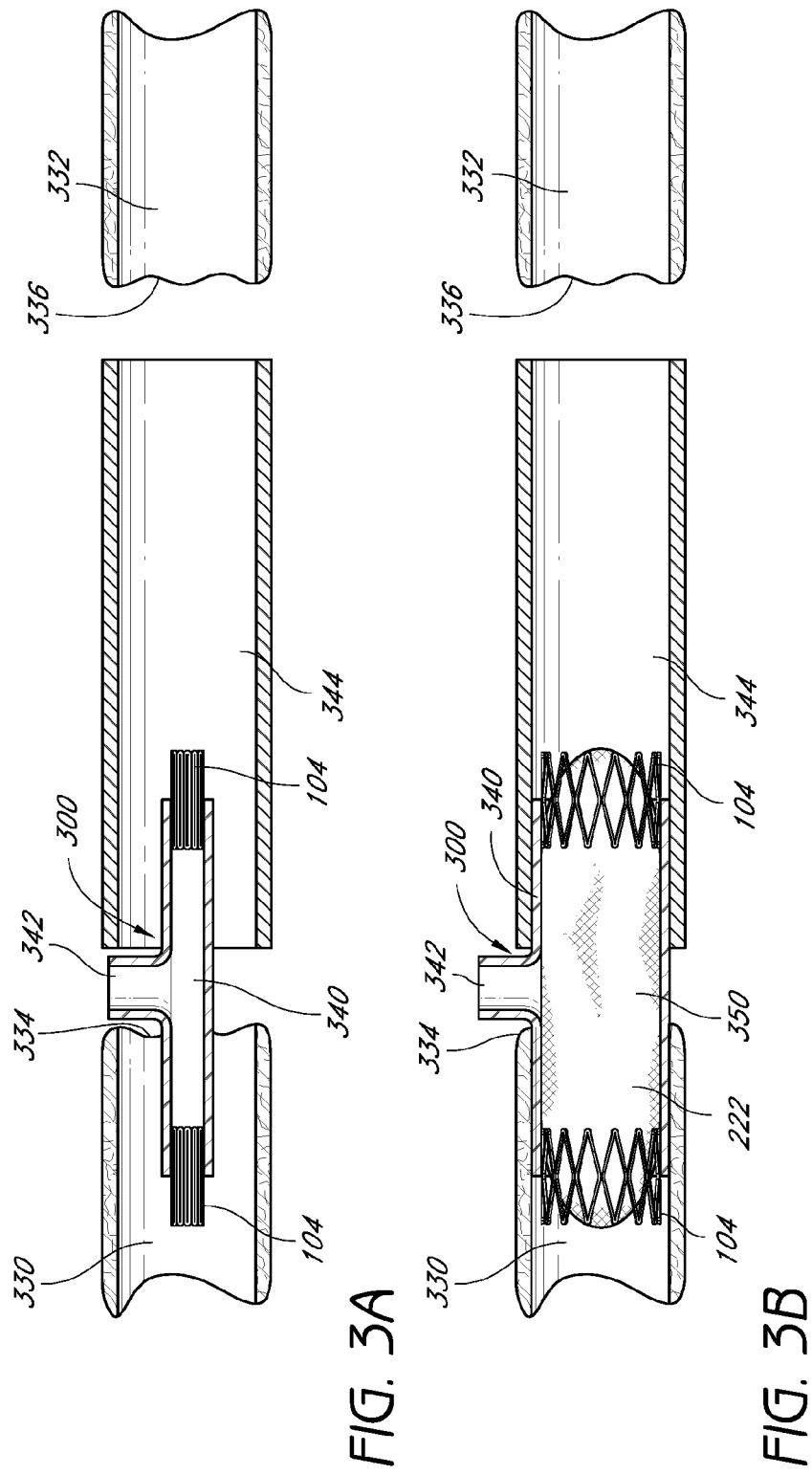

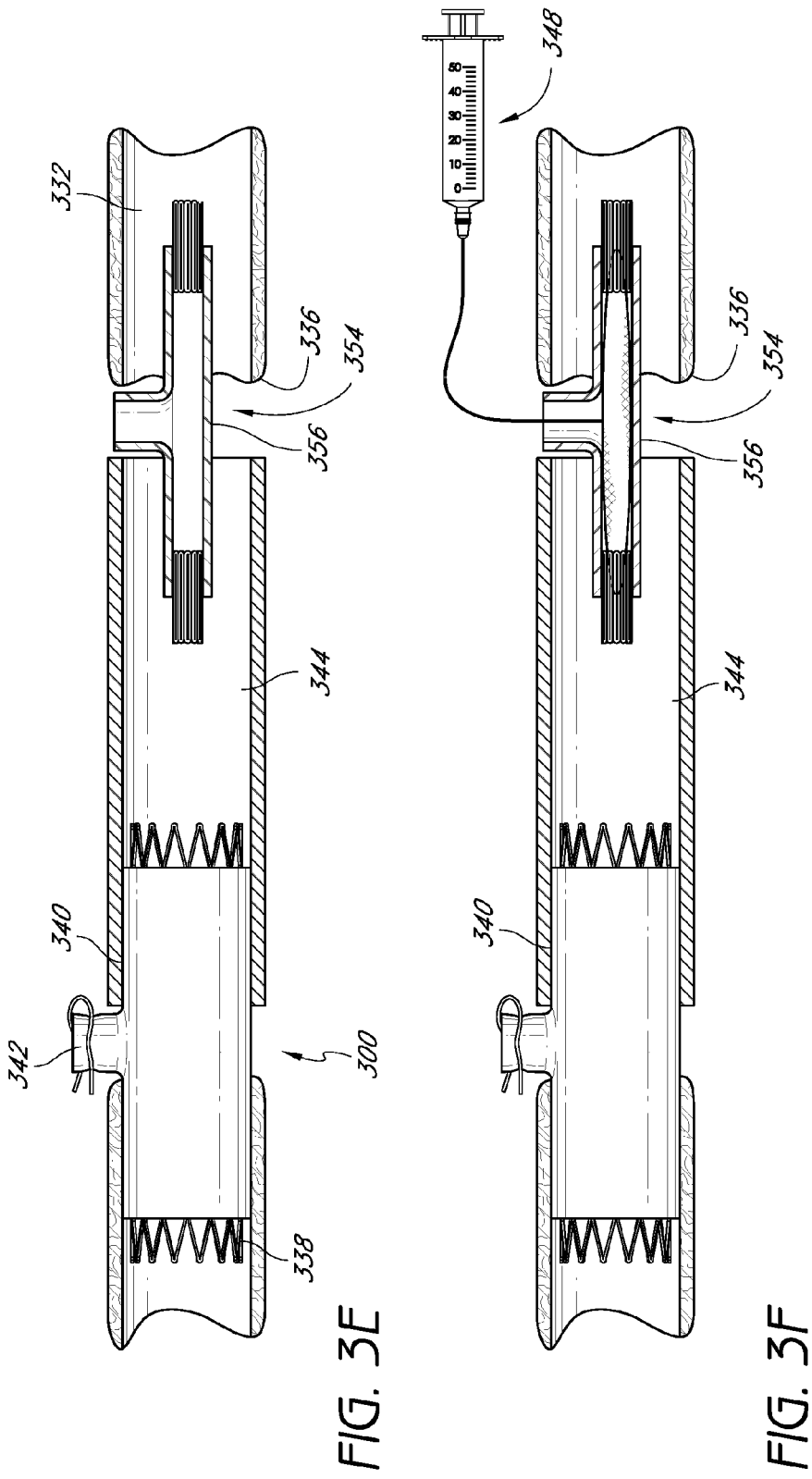

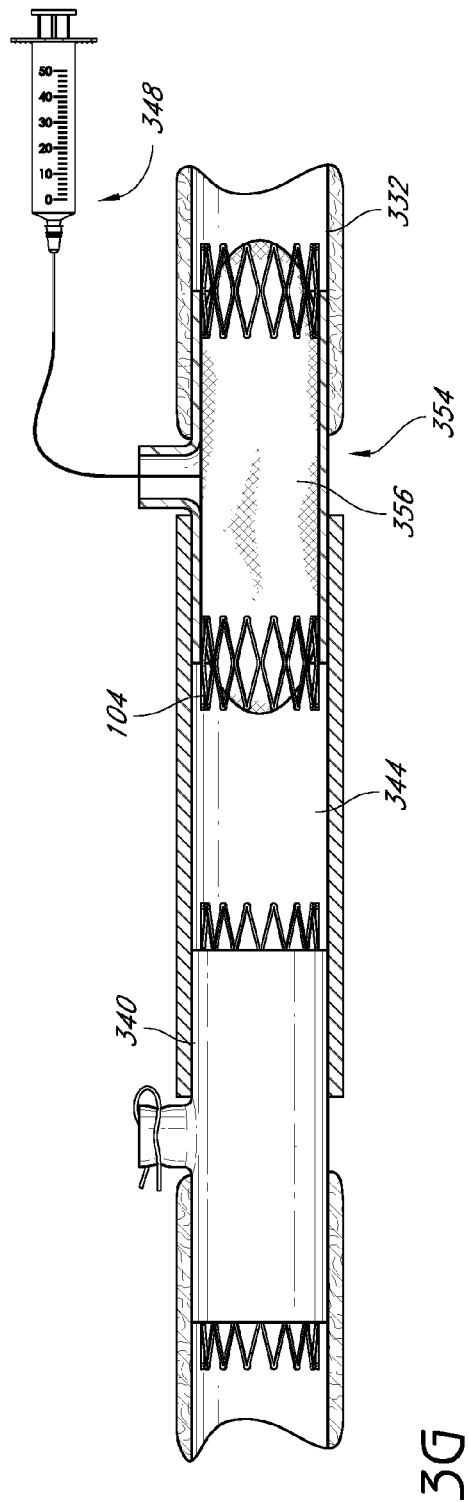
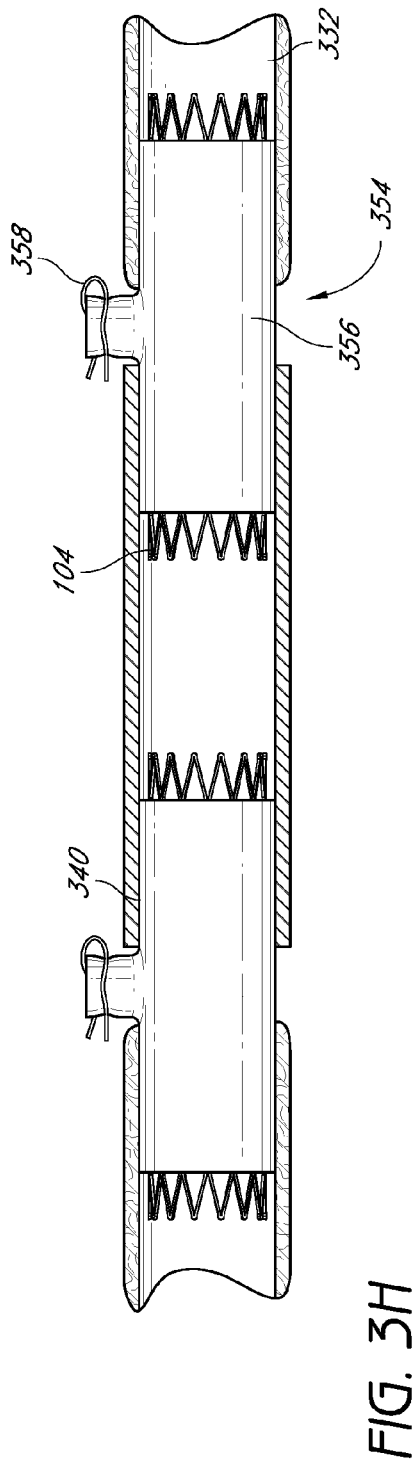
FIG. 3G
FIG. 3H

DEVICES, SYSTEMS, AND METHODS FOR REPAIR OF VASCULAR DEFECTS

PRIORITY CLAIM AND CROSS-REFERENCE TO RELATED APPLICATIONS

This application claims the benefit of priority of U.S. Provisional Application No. 61/587,570, which was filed Jan. 17, 2012, the entire contents of which are hereby incorporated herein by reference and should be considered part of this specification.

This application is a continuation-in-part of U.S. application Ser. No. 12/819,949, which was filed Jun. 21, 2010, which is a continuation-in-part of PCT Application No. PCT/US2008/087849, which was filed on Dec. 19, 2008 and published on Jul. 2, 2009 as WO 2009/082718, the entire contents of which are hereby incorporated herein by reference and should be considered part of this specification. The above-referenced PCT application claims prior to and the benefit of U.S. Provisional Application Nos. 61/016,400 and 61/055,428, filed Dec. 21, 2007 and May 22, 2008, respectively, each titled "Devices, Systems, and Method for Repair of Vascular Defects," which are also hereby incorporated by reference in their entirety, including without limitation, the descriptions of the vascular devices and the associated methods of use to repair vascular defects.

BACKGROUND

Field

Embodiments of the disclosure relate to the field of vascular prostheses for repairing a vascular defect.

Description of Related Art

Large vascular defects arise when all or a portion of a vessel is severed or damaged to the extent that the vessel loses functionality as a conduit through which body fluid, such as blood, can flow. Blood vessels, for example, may be severed or lacerated traumatically in an accident or under controlled, surgical conditions such as amputation, coronary artery bypass grafting, or construction of other anastomoses. Rapid fluid loss and, in the case of circulatory defects, loss of tissue perfusion is often characteristic of large vascular defects. The potential fluid loss in emergencies and during surgery can be life-threatening unless brought under control quickly and effectively. Furthermore, escaping fluid can obscure the view of the working surgical site.

To minimize fluid loss from large vascular defects, harvested grafts are connected to bridge, or shunt, separate portions of the natural vasculature, including portions from which fluid is being, or is expected to be, lost. Such grafts serve to restore functionality to the damaged vessels by acting as a bridge or tube through which fluid can flow. This approach, however, is time consuming and often not possible during exigent circumstances, such as those encountered in an emergency room.

SUMMARY OF THE INVENTION

An aspect of the present disclosure relates to methods and systems suitable for repair of both small and large blood vessel defects. Some embodiments are devices having an expanded state and an unexpanded state. Various embodiments include bidirectional balloon expandable covered stents for traumatic vascular defects. Some embodiments comprise a stented member, an elongate graft member and an access portion connected to the elongate graft member, which may or may not be comprised of the same materials.

In some embodiments, the access portion is elliptically shaped so as to minimize shear stress on blood making its way through the device. Some embodiments have a first side, a second side, and a middle portion which extends between the first side and the second side. In some embodiments, the device is sized such that it can extend across a ruptured portion of a vessel and when in its expanded state can seal the vessel so that none of the fluid flowing through the vessel escapes as it flows past the region of intersection between the device and the vessel.

In some embodiments, the device is comprised of a PTFE graft bonded to one or more balloon expandable stents, although the graft may be made of any other material suitable for repairing a vascular defect. Similarly, the stent material may be a metal, a metal alloy, or other material or combination of materials and/or biomaterials suitable for implantation or for use in other biomedical applications. Such materials are well known in the art. The stent may be of any suitable material and configuration, including drug-eluting, polymeric, composite metal, annularly shaped, and ovalularly shaped.

In some embodiments, the device is further comprised of an access portion through which a balloon catheter can access and manipulate the interior walls of the device that can serve as a fluid conduit, or any other conduits of which the device is comprised in any of its variations. Such variations include, for example, pockets within a conduit that contain fluids to be released at a time subsequent to implantation or positioning into the vessel undergoing treatment. The access portion need not be located in the center of the device. Further, it may extend from the device at a near 0° angle or any other suitable angle relative to a longitudinal axis through the shunt. It may extend from or into the device.

According to one aspect of the disclosure, a vascular repair device is provided that comprises at least one vascular support element, such as a stent made of stainless steel, cobalt-chromium alloy, or Nitinol, and at least one graft coupled to the vascular support. According to some embodiments, the vascular support element is coupled to an inner surface of the graft. According to some embodiments, the vascular support element is coupled to an outer surface of the graft. According to some embodiments, the vascular support element is coupled to outer and inner surfaces of the graft. According to some embodiments, the vascular support element is coupled to the graft between an outer surface and an inner surface of the graft.

The vascular support element may support the graft either along its entire length or along only a portion of its length. One aspect of the invention involves recognizing that the length of the portion of the support element (e.g., a stent) supporting the graft (e.g., the portion of the stent attached to the graft) wall can be greater than or equal to the maximum diameter of the graft lumen when in an expanded state. Preferably, the ratio of the length of a vascular support element that is supporting the graft from within (e.g., attached to) to the maximum diameter of the graft lumen may be in the range of 1:1 to 2:1. In some embodiments, that ratio is in the range from 1:1 to 2.5:1. In other embodiments, that ratio is in the range of 1:1 to 3:1 or higher. While 1:1 is the preferred ratio, the ratio in other embodiments can be slightly less than 1:1.

The graft includes an access portion through which a surgeon can access the vascular support. The device is suitable for placement and/or introduction through a vascular defect into the vessel lumen either directly or over a guidewire. The vascular support expands to engage at least one portion of a vessel at a location removed from a vascular defect to couple the graft to the vessel. In some embodiments, the graft has a configuration suitable to inhibit fluid leakage from the vessel through the defect.

The graft can be of synthetic or biologic materials, or a combination of both. The graft may also include one or more therapeutic agents. Such agents could include, for example, but without limitation, vasodilators, vasoconstrictors, hydrophobic or hydrophilic coatings and/or materials, anticoagulant coatings and/or materials such as heparin, controlled-diffusion polymers, antibiotic materials, antiproliferative materials, agents that induce vascular proliferation and/or remodeling, immunosuppressive drugs, proteins, carbohydrates, self-assembled monolayers, stainless steel, or any other suitable agent that provides a therapeutic or beneficial effect. Such agents can be coated, bonded, or otherwise integrated into or with the graft material. Additionally, such agents can elute from the inside of the graft, from the outside of the graft, from both the inside and outside of the graft, or from only select regions of the graft. In some embodiments, the graft also is formed of a material that can be sutured. Thus, a generally fluid-tight seal or interface can be obtained between the graft and a vessel.

In some embodiments, a balloon can be inserted through the access portion in the graft and placed within the vascular support. By inflating the balloon, the at least one vascular support element can be expanded to make sealing contact with the vessel walls. In other embodiments, the at least one vascular support element can comprise a self-expanding material, such as Nitinol (Nickel Titanium Naval Ordinance Laboratory) and/or an electroactive polymer and/or can have mesh-like or stent-like structure. The vascular support also can include therapeutic agents in addition to or alternative to a graft which elutes such agents.

According to another aspect of the disclosure, there is provided a vascular repair device comprising at least two vascular support elements and at least one graft extending between the vascular support elements. The graft includes at least one access portion through which one or more of the vascular support elements can be accessed. Each vascular support element is expanded to engage a portion of the vessel at a location remote from a vascular defect to couple the graft to a vessel. The graft has a configuration suitable to inhibit fluid leakage from a vessel through a defect. As noted before, the graft may be, for example, synthetic or biologic. Notably, in other embodiments, the function of the two support elements can be served by a single support element.

In some embodiments, the graft can be advantageously configured to repair a vascular defect where a section of a vessel has been completely severed between a first vessel portion and a second vessel portion. Some embodiments allow linkage of more than two severed vessel portions. In some embodiments, the graft preferably has a sufficient length and shape to extend between the first and second vessel portions. One of the vascular support elements is inserted into the first vessel portion to couple the graft thereto, and another vascular support element is inserted into the second vessel portion to couple the graft to the second vessel portion. In some embodiments, the vascular support elements are expandable by balloon or are fully or partially self-expanding, and can be delivered along with the graft or separately delivered and subsequently coupled to the graft. In some embodiments, one or more of the vascular support elements and/or the graft can be biodegradable, such as in embodiments that allow for vascular remodeling/repair sufficient to eventually render the repaired vessel effective for conducting fluid without assistance of a graft member. Where the graft serves the function of a healthy, normal vessel wall, of course, it preferably is not biodegradable.

According to an additional aspect of the disclosure, a vascular repair system is provided comprising at least one vascular support element defining a proximal flow orifice and a distal flow orifice, at least one biocompatible graft, and at least one sealing member. The graft includes an access portion through which access to the vascular support can be obtained. The graft also has a suitable configuration to provide generally a barrier to fluid leakage from a vessel having a defect. The sealing member closes the access portion of the graft so as to provide a barrier to fluid transfer through the access portion of the graft once implanted. In some embodiments, the access opening is sized to permit placing a balloon within a vascular support element to expand the vascular support element.

A preferred embodiment of repairing a vascular defect is also provided that involves providing a vascular graft with one or more vascular support elements coupled to the graft. Once access to a vascular defect has been obtained, a vascular support element is inserted through the defect in a vessel and positioned near competent tissue. The graft is configured to bridge the defect, thereby extending between at least two sections of vessel. An expandable member (e.g., a balloon) is inserted through an access port in the graft and delivered to a position lying within each vascular support, separately or in tandem. Expansion (e.g., by inflation) of the expandable member causes the vascular support elements to engage the competent tissue, preferably in a circumferential manner. The vascular support elements may each be expanded separately or together, depending on the application and circumstances. The expandable member is then withdrawn from the graft and the access port is closed. Thus, the expandable member anchors the graft to the vessel and the defect is repaired.

Another preferred embodiment of repairing a vascular defect is also provided that involves a vascular graft, which is self-expanding or is expanded by an internal force (e.g., by an expandable scaffolding). Additionally, in some embodiments, the graft can include a conventional septum side port—in addition to or integrated with an inflation port—to provide additional access to the central blood flow through the graft when in situ.

In other embodiments, other types of vascular coupling devices can also be used as an alternative to or in addition to wire support members (e.g., stent-like structures). For example, an additional way to attach the graft to the ruptured vasculature involves using one or more inflatable cuffs at each end of the graft to secure the graft to the vascular wall. One or more of the cuffs can be inflated using an inflation port that is either internally or externally accessible.

Another aspect of the disclosure involves a shunt device for shunting a traumatically disrupted vessel. The shunting device comprising a body having at least one lumen extending therethrough between first and second ends of the body. At least a segment of the body is expandable from a first state to second, expanded state. In the expanded state, the body segment is generally equal in size to a dimension across the vessel. An access port provides access into the lumen and is disposed between the first and second ends of the body. The access port is sized to receive at least a portion of a balloon for expanding at least the body segment to the second state.

BRIEF DESCRIPTION OF THE DRAWINGS

FIG. 3A shows a first stented member of a vascular repair device extending into a ruptured vessel portion at one end and into a graft member at its other end.

FIG. 3B shows an expandable member inserted into a portion of the first stented member.

FIG. 3E shows a device with a second stented member extending into a second end of a graft member at one end and into a ruptured portion of a vessel portion at its other end.

FIG. 3F shows a device with an expandable device in a substantially unextended configuration extending through the second stented member.

FIG. 3G shows the portions of the embodiment shown in FIG. 2F with the second stented member in an expanded configuration.

FIG. 3H shows an embodiment sealed with a clamp placed over the second stented member.

DETAILED DESCRIPTION OF THE DRAWINGS

Figure 1A:
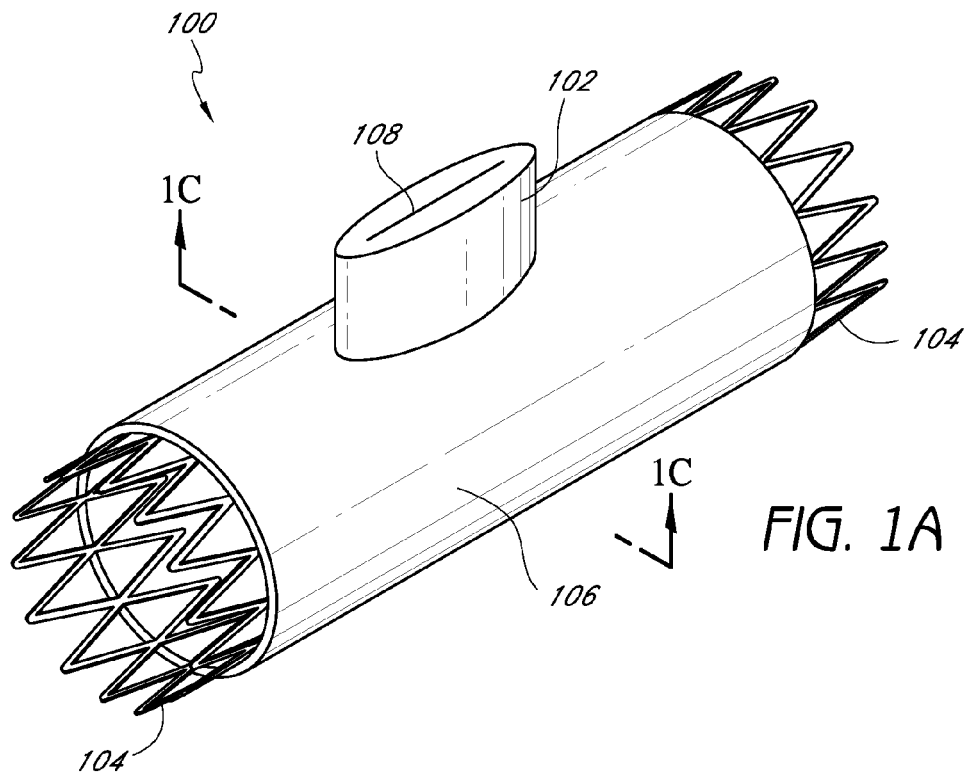
FIG. 1A shows a vascular repair device configured according to an embodiment.

FIG. 1A shows an embodiment of a vascular prosthetic device 100 in its expanded state designed for endoluminal applications. The device 100 in this embodiment comprises a sleeve or graft portion 106 supported at least at its ends by a plurality of tubular wire support members 104. While in the illustrated embodiment, the graft portion 106 extends between the support members 104, in other embodiments, a single support member 104 can be used that extends through the graft portion 106. An access portion or port 102 communicates with a lumen 108 of the graft portion 106. The access portion 102 is shown in an unbiased configuration wherein the access portion 102 is compressed upon itself to form a seal.

The graft portion 106 in the illustrated embodiment has a tubular shape and defines at least one lumen 108. The lumen 108 terminates at the ends of the graft in first and second openings 108a, 108b. The graft portion 106, however, can have other configurations in other embodiments. For example, but without limitation, the graft portion can have a Y-shape, a T-shape or an X-shape with a plurality of openings (e.g., three or greater). In some embodiments, all of the openings may communicate with one another, and in other embodiments only certain openings communicate with one another.

In some embodiments, at least some of the ends of the graft portion 106 do not include a corresponding support element 104 and instead are designed to be coupled with a corresponding end of another vascular prosthetic device. In other embodiments, the support elements 104 are used to interconnect a plurality of vascular prosthetic devices. In this manner, a plurality of vascular prosthetic devices can be linked together to repair, replace, bypass or supplement the physiologic vasculature of a patient. The linking of the prosthetic devices together can be done before being placed in a patient's body or during placement within a patient's body.

The graft 106 may be formed from any of a variety of synthetic polymeric materials, or combinations thereof, including PTFE, PET, PE, nylon, Urethane, Dacron, polyester or woven textiles. The material of the graft 106 preferably has a relatively low inherent elasticity or low elasticity until expanded to or beyond its intended expanded diameter.

In the illustrated embodiment, the graft 106 is situated concentrically outside the support members 104. However, other embodiments may include a sleeve situated instead concentrically inside one or both of the support members or on both the inside or outside of at least one of the support members 104. Alternatively, one or both of the supports may be embedded within the graft.

The support members 104 are attached to the graft 106, either on the inside or outside surfaces thereof, by any of a variety of ways, including laser bonding, adhesives, clips, sutures, dipping or spraying or other means, depending upon the composition of the graft and the overall graft design.

In the illustrated embodiment, a middle section of the graft 106 is unsupported by the support members 104. This permits the graft 106 to be folded or bent so as to be more easily inserted into a partially ruptured vessel or a vessel hole. In other embodiments, increased flexibility of the prosthetic device can also be obtained by removing sections of the wire support between the ends of the device (for example, by forming gaps between wire segments along the longitudinal axis of the device and/or by forming gaps around the circumference of the tubular wire structure). In some embodiments, flexible longitudinal struts can be used to link together the two or more support members 104, which are spaced apart along the longitudinal axis of the device.

Figure 1B:
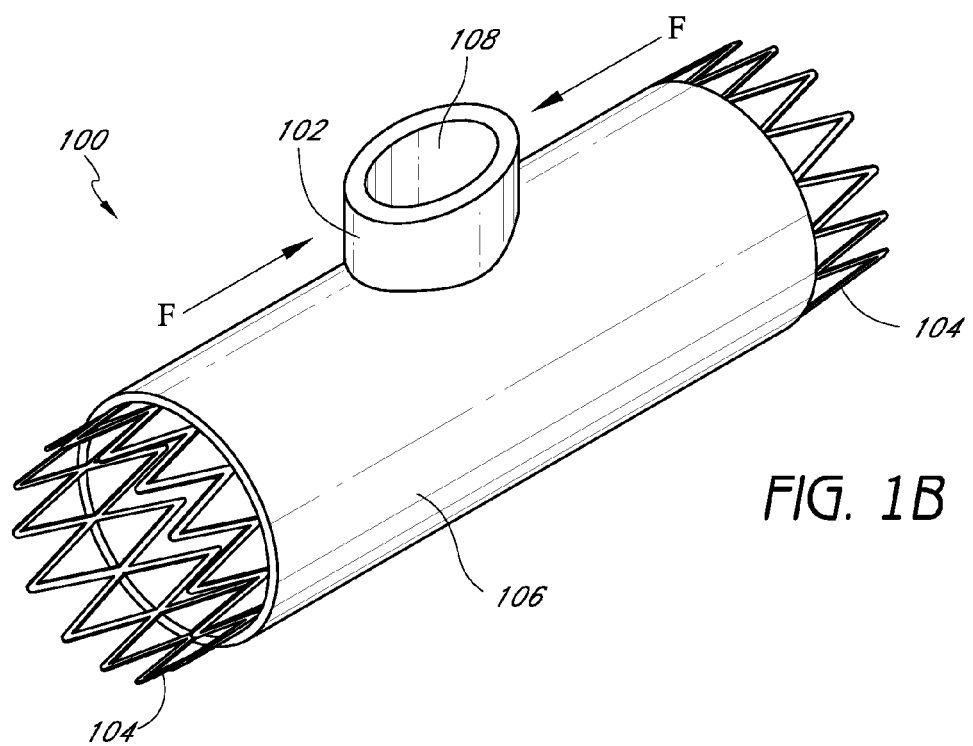
FIG. 1B shows a vascular repair device configured according to an embodiment.

In the illustrated embodiment, the support member 104 has a stent-like structure that is capable of being expanded for a compact state (e.g., collapsed state) to an expanded state. As best seen in FIGS. 1A and 1B, the support member 104 comprises a wire frame structure with a generally tubular appearance at least when in the expanded state. The wire frame structure has linked wire segments that allow it to be expanded in diameter in situ.

The support members 104 and graft portion 106 are cylindrical and hollow generally to match the shape of a typical blood vessel. However, the stent members 104 and graft portion 106 may be shaped differently depending on the requirements of a particular surgical protocol or requirements of the particular application, as discussed in greater detail below. The access portion 102 and access portion conduit 108 are elliptical in shape so as to minimize shear forces acting against blood cells traveling through the vascular access device 100 along the inner wall 107.

FIG. 1B shows a vascular access device 100 as shown in FIG. 1A wherein the access portion 102 has been manipulated by force F so as to separate the walls of the access portion conduit 108 and to provide an open pathway for communication between the environment outside the graft portion 110 and the environment inside the graft portion (not shown). When force F is removed from the access portion 102, the access portion returns to the configuration shown in FIG. 1A. Thus, some embodiments of the present inventions include a deformable, self-biased access portion 102 that deforms under force and returns to its resting configuration when such force is released. While not shown, other embodiments of the device 100 can include a valve situated at the access portion 102 or communicating therewith to permit medical instruments to be passed into, manipulated in, and removed from the device through the access portion 102 with minimal fluid (e.g., blood) loss.

Figure 1C:
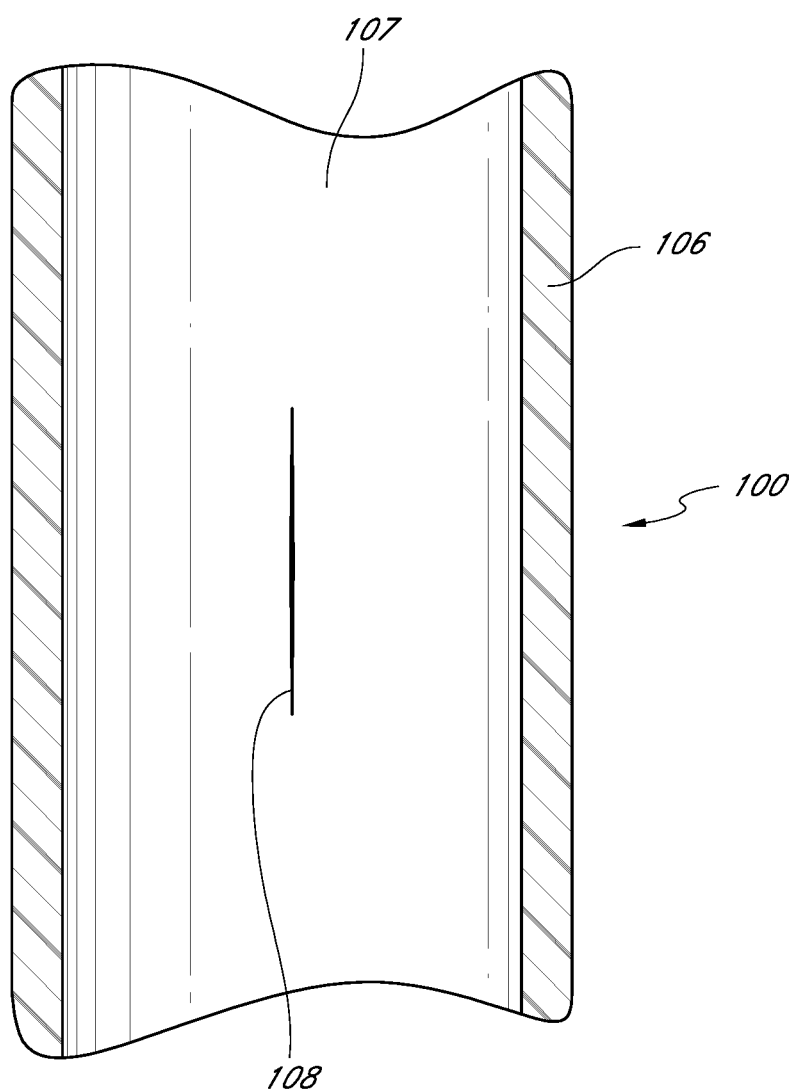
FIG. 1C shows a cross-sectional view of a portion of a vascular repair device configured according to an embodiment.

FIG. 1C shows a portion of the vascular access device in the self-sealed configuration of FIG. 1A. Due at least in part to its elliptical shape, the access portion conduit 108 is closed upon itself along a generally straight line. Furthermore, the elliptical shape and, in some embodiments, the material composition of the access portion 102 discourage folding along the inner wall 107 of the vascular access device 100. This configuration helps ensure that irregularities, and the shear forces on body fluids flowing along the inner walls of the device 100 and opportunities for fluid components to pool, clot, stagnate, or aggregate that such irregularities are known to cause are minimized.

Figure 1D:
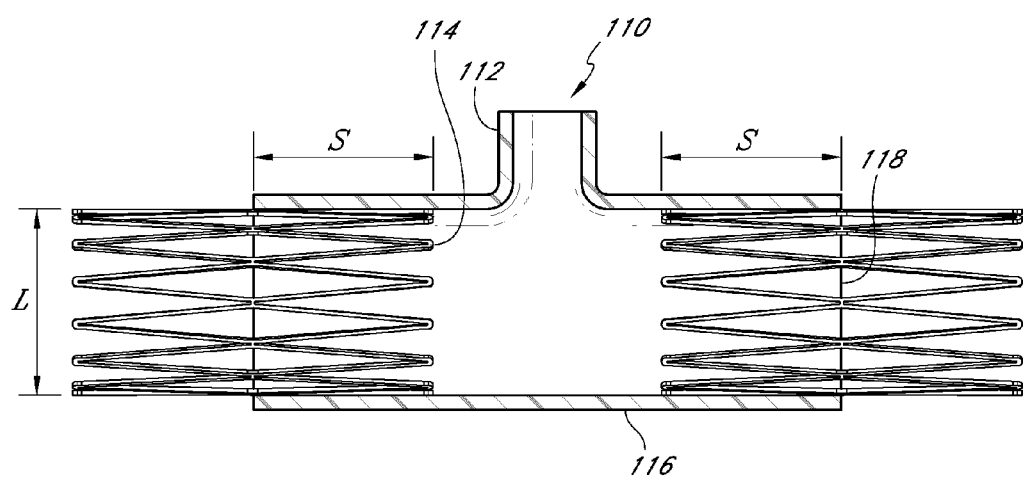
FIG. 1D shows a vascular repair device configured according to an embodiment.

FIG. 1D shows a cross-sectional view of an embodiment of a vascular prosthetic device 110 designed for endoluminal applications in its expanded state. The device 110 in this embodiment comprises a sleeve or graft portion 116 supported at least at its ends by a plurality of vascular support members 114. While in the illustrated embodiment, the graft portion 116 extends between the vascular support members 114, in other embodiments, a single support member can be used that extends through the graft portion 116. An access portion or port 112 communicates with a lumen 118 of the graft portion 116. The maximum diameter of the graft lumen is labeled L. In some embodiments, the maximum diameter of the lumen can be anywhere from 6 mm to 1.2 cm. The length of the vascular support element supporting from within (e.g., attached to) the graft is labeled S. Thus, the ratio of the length of the vascular support element 114 supporting the graft 116 from within to the maximum diameter of the graft lumen 118 can be expressed as S:L.

The length of the portion of the vascular support element 114 supporting the graft wall S can be greater than or equal to the maximum diameter of the graft lumen L when in an expanded state. Preferably, the ratio of the length of a vascular support element 114 that is supporting the graft from within S to the maximum diameter of the graft lumen L may be in the range of 1:1 to 2:1. In some embodiments, that ratio is in the range from 1:1 to 2.5:1. In other embodiments, that ratio is in the range of 1:1 to 3:1 or higher. While 1:1 is the preferred ratio, the ratio in other embodiments can be slightly less than 1:1.

Figure 2A:
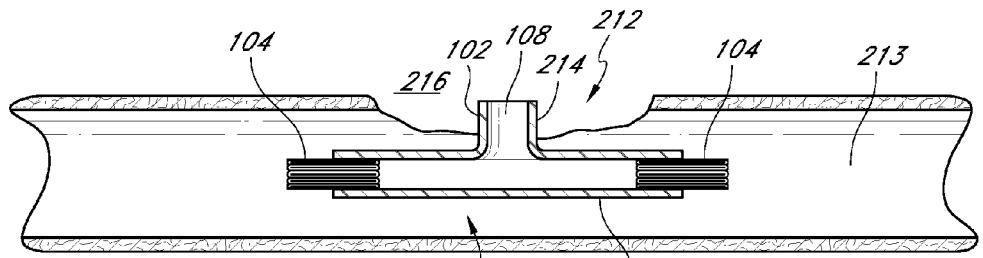
FIG. 2A shows a vascular repair device inserted into a ruptured blood vessel.

FIG. 2A illustrates an embodiment of the vascular access device 100 in the repair of a small vascular defect 212. A vascular access device 100 is situated in a blood vessel 213 such that the device 100 extends across a ruptured portion of the vessel 212. The device 100 is further situated such that the access portion 102 of the graft 106 provides access to the elongate graft portion 106 from the surgeon's working environment 216. The device 100 may be so situated by inserting one end of the graft 106 into the vessel 213 through the ruptured portion of the vessel 212 and simultaneously or subsequently similarly inserting the other end of the graft 106. Alternatively, the device 100 may be inserted over a guidewire. The device of the present embodiment is comprised of a T-piece 214 and an elongate graft portion 106. Although the intersection between the T-piece 214 and the elongate graft portion 106 is shown such that these portions are perpendicular to one another, they may be manufactured or, in some embodiments, manipulated to intersect at various angles ranging from nearly 0° to nearly 90° and may further be comprised of materials or design that allows a surgeon to easily adjust the angles of intersection between the T-piece and various portions of the graft portion 106. For example, the device could take on a Y-shape or an M-shape rather than a T-shape. Furthermore, the access portion 102 need not intersect the graft portion 106 at a constant angle.

The present embodiment further comprises at least one stent portion 104 to provide support to openings 214 and the elongate graft portion 106. The stent portion 104 is coupled to the elongate graft portion 106 such that the stent portion can affect expansion of the elongate graft portion 106. The stent portion 104 may extend along the length of the graft 106 and extend out the openings 214 of the graft 106. The stent portion 104 may be integral with, intermeshed with or embedded within, or separate from the graft portion 106. The stent portion 104 may comprise two stent portions or more, and at least a portion of the at least one stent portion 104 can be attached or otherwise coupled to the outside or the inside of the graft 106.

Figure 2B:
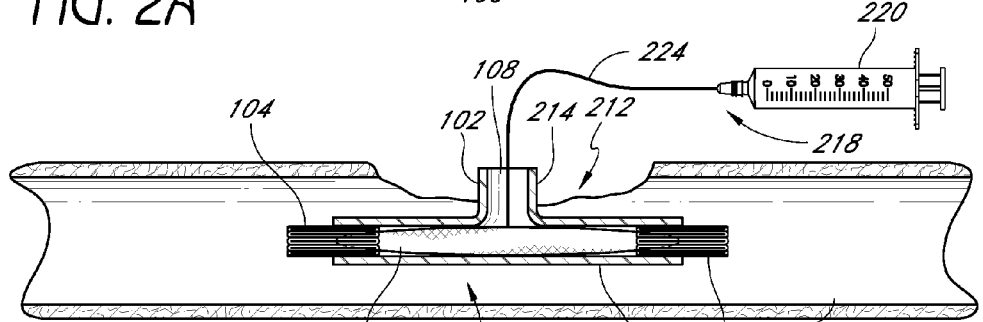
FIG. 2B shows a vascular repair device inserted into a ruptured blood vessel and an expandable member inserted into the device.

FIG. 2B shows a vessel 213 and a vascular access device 100 and further shows a balloon catheter 218 comprised of a pump portion 220 and a catheter. The catheter 218 is comprised of a balloon portion 222 in fluid communication a tube portion 224 and a pump portion 220. The catheter 218 may be any suitable catheter configuration. The balloon portion 222 extends into the elongate graft member 106 such that it pushes the graft member 106 into an expanded configuration upon expansion.

Figure 2C:
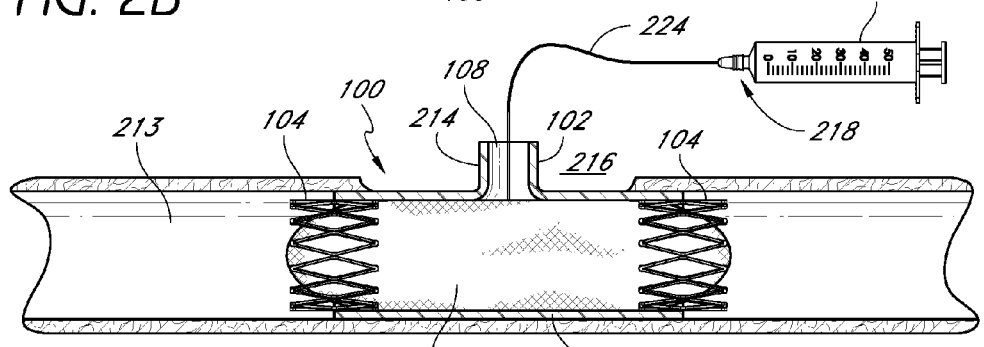
FIG. 2C shows a vascular repair device in an expanded state.

The balloon catheter 218 is positioned inside the graft 106 through the conduit 108 and extends through the access portion 102 such that when the balloon is expanded it forces the graft 106 to expand toward the vessel wall 213 and to thereby create a seal around the ruptured portion of the vessel 212 between the ruptured portion 212 and the graft 106 as shown in FIG. 2C where the vascular access device 100 is in an expanded configuration and extends across a ruptured wall of the vessel 213. The access portion 102 extends out of the ruptured wall into the environment accessible to the surgeon 216.

Figure 2D:
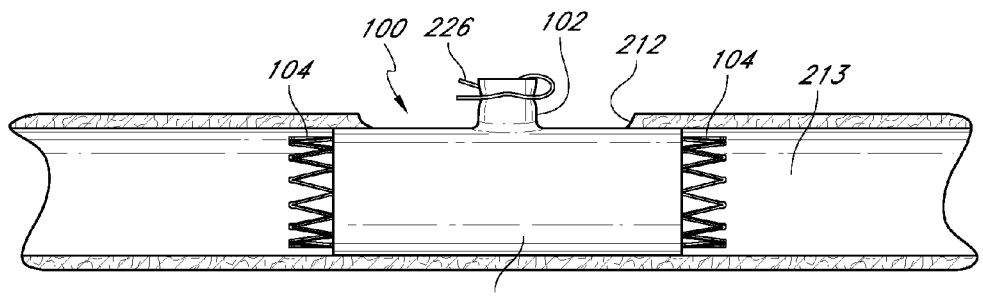
FIG. 2D shows a vascular repair device in an expanded state and sealed with a clip.

FIG. 2D shows a vascular access device 100 in an expanded configuration and sealingly engaged with a vessel 213 along ruptured wall 212 with a clip 226 sealing the access portion 102 of the graft member 106. The device 100 is expanded such that the at least one stent portion 104 circumscribes the inner vessel wall 213 and thereby creates a tunnel through which fluid in the vessel can pass. The balloon (not shown) is removed and the access portion 102 of the graft 106 is sealed using a clip 226 or other suitable sealing means. Such sealing means could comprise, for example, adhesion, heat bonding, closure of a valve provided on an access portion of a PTFE graft, self-sealing, or any other suitable means identifiable by one of ordinary skill in the art. The seal may be reversible such that before or after the seal is originally applied, the access port 102 can be used, for example, for passage of a medical implement such as an embolectomy catheter, infusion of medications including anticoagulants or thrombolytics, infusion of contrast for imaging, and as access for a guidewire or other vascular and/or surgical device.

Figures 3C, 3D:
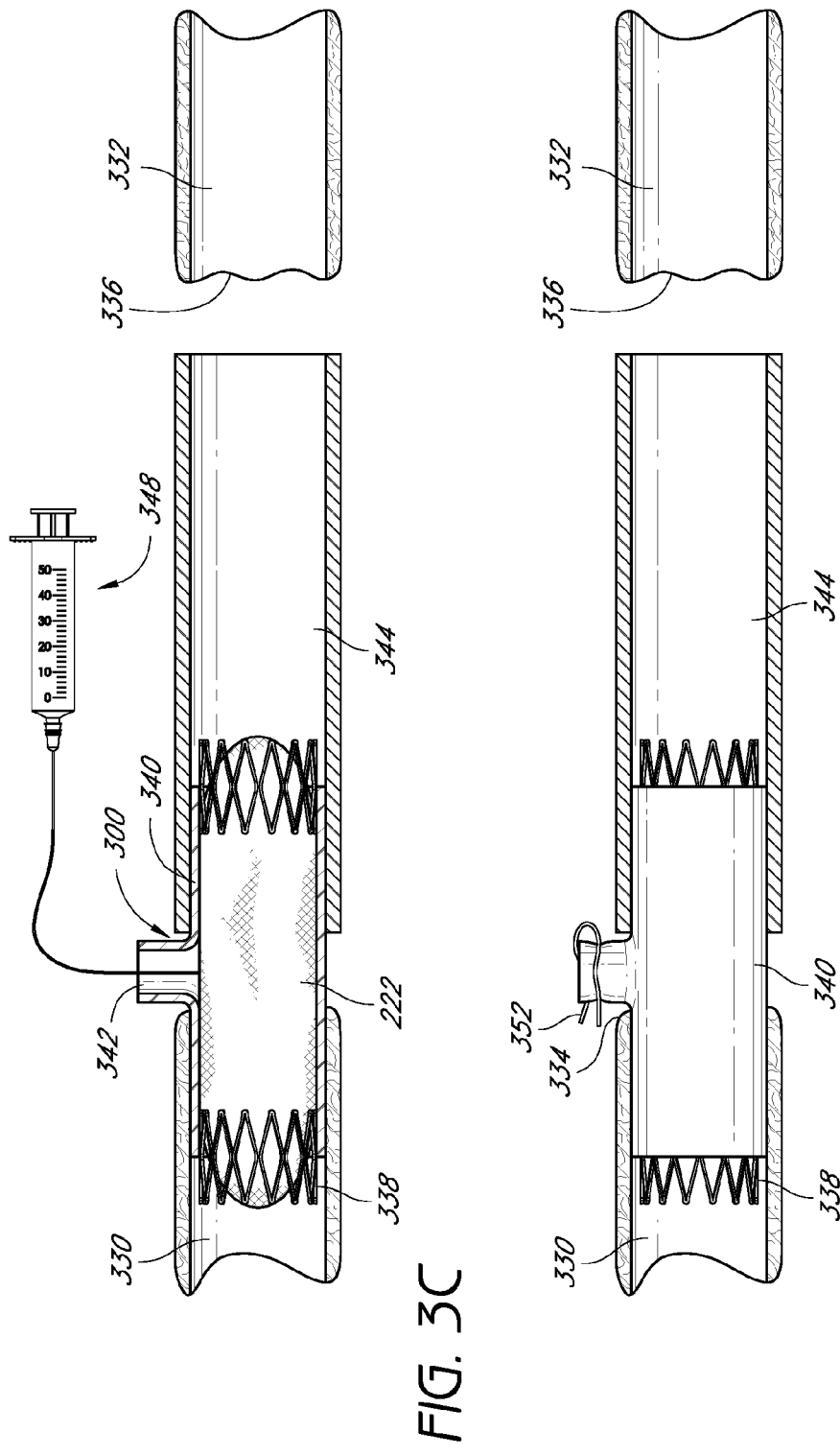
FIG. 3C shows an expandable member and the first stented member in an extended configuration such that it prevents fluid from escaping through the ruptured portion of the first vessel portion.
FIG. 3D shows a first stented member sealed with a clip.

FIGS. 3A-3H show the device employed to repair of a large vascular defect. As shown in FIG. 3A, a defect is comprised of two vessel portions 330, 332, a first portion 330 and a second portion 332. The first portion 330 comprises a first ruptured wall 334, and the second portion 332 comprises a second ruptured wall 336. The vascular access device comprises a first stented member 330 comprising a first graft portion 340 that is further comprised of an access portion 342, a second graft portion 344 extending, or configured to extend, between the first ruptured wall 334 and the second ruptured wall 336, and a second stented member 354 as shown in FIG. 3E that is substantially similar to the first stented member 300.

With further reference to FIG. 3A, the first stented member 300 is inserted into the end of the vessel portion 330 through the vascular defect 334 such that the elongate portion of the first stented member 340 extends both into the vessel 330 through the vascular defect 334 and out of the ruptured wall, or vascular defect 334, and into the second graft portion 344. The portion of the elongate portion of the graft 340 extending out of the ruptured wall 334 fits within the second graft portion 344.

With reference to FIG. 3B, a balloon catheter (not shown) is inserted into the access portion 342 and the stent members 104 and graft portion 340 are expanded via the balloon catheter 348 as shown in FIG. 3C. The balloon 222 is inflated until there is a seal between the graft 340 and the vessel 330 and until substantially no fluid escapes from between the ruptured wall 334 and the elongate graft portion 340 of the first stented member 300. The balloon catheter 348 may employ various known techniques, such as injection of saline solution, to cause expansion of a balloon 350 or another expandable device capable of applying enough force to a stented member 300 and create a seal against a vessel wall.

FIG. 3C shows the balloon catheter 348 within the first stented member 300. The first stent member 300 is in an expanded configuration. The second graft member 344 extends from the first stented member 300. The first stented member 300 is placed in sealing engagement with the first vessel portion 330 and with the elongate graft member 340. The balloon 222 may be removed as shown in FIG. 3D and the access portion may be sealed using a clamp 352 or any other suitable method of preventing fluid from escaping between the ruptured vessel wall 334, the second graft portion 344 and the elongate graft member 340.

FIG. 3E shows a second stented member 354 inserted into the second graft member 344 and the second ruptured vessel wall 336 such that a first end of the second elongate graft portion 356 extends into the second graft portion 344 and a second end extends into the second ruptured vessel wall 336. The balloon inflation process described above is repeated such that the second stented member 354 sealingly engages with the second vessel wall portion 332 as shown in FIG. 3G after passing through the intermediate step shown in FIG. 3F and described above to complete a sealed flow path as shown in FIG. 3G defined by the first stented member 300 and second stented member 354 and the second graft portion 344. Finally, the balloon catheter is removed as shown in FIG. 3H, and the second device is sealed at its access portion using a second clamp 358 or any other suitable method of sealing.

As understood from the above description, each of the shunt devices illustrated in FIGS. 1A-3H can be used to quickly repair damages or ruptured vessels. The inflation balloon can be included with the shunt device in a surgical kit and can be preassembled with the shunt so that a surgeon need only place the shunt device within a vessel or between vessel segments and inflate the balloon to place the device. The balloon can then be deflated, removed through the access portion and disposed. The surgeon can then further close off the access portion by tying it closed or by using a provided clamp, clip, tie, or other sealing means as described above. Once in place, the device shunts body fluid across the damaged vascular structure and can remain in place temporarily until replaced by a more permanent solution or for an expended period of time, including permanently.

In other embodiments, the graft portion can be self-expanding or can be expanded by an internal force (e.g., by an expandable scaffolding). If the graft sleeve and/or an internal mechanism is self-expanding, the inflation port (e.g., a side channel or valve) can be omitted from such embodiments. Additionally, in some embodiments, the graft can include a conventional septum side port—in addition to or integrated with an inflation port—to provide additional access to the central blood flow through the graft when in situ.

Other vascular coupling devices can also be used in some embodiments as an alternative to or in addition to the wire support members specifically described above. For example, an additional way to attach the graft to the ruptured vasculature involves using one or more inflatable cuffs at each end of the graft to secure the graft to the vascular wall. By using inflatable cuffs, a longer "landing zone" against the vascular wall can be obtained in comparison to the stents described above. One or more of the cuffs can be inflated using one or more inflation ports that are either internally or externally accessible.

Although this disclosure has been disclosed in the context of certain preferred embodiments and examples, it will be understood by those skilled in the art that the present disclosure extends beyond the specifically disclosed embodiments to other alternative embodiments and/or uses of the disclosure and obvious modifications and equivalents thereof. In particular, while the present vascular access devices, systems, and methods have been described in the context of particularly preferred embodiments, the skilled artisan will appreciate, in view of the present disclosure, that certain advantages, features and aspects of the system may be realized in a variety of other applications, such as sealing of conduits within a mammalian body other than blood vessels. Additionally, it is contemplated that various aspects and features of the disclosure described can be practiced separately, combined together, or substituted for one another, and that a variety of combination and subcombinations of the features and aspects can be made and still fall within the scope of the disclosure. Thus, it is intended that the scope of the present disclosure herein disclosed should not be limited by the particular disclosed embodiments described above, but should be determined only by a fair reading of the claims.

What is claimed is:

1. An expandable shunt for shunting a disrupted vessel, comprising:
   a graft defining a first lumen having a maximum expanded-state diameter and extending between first and second ends of the graft;
   at least one expandable support element supporting a length of the graft from within near at least one of the first and second ends of the graft;
   a side channel defining a second lumen and configured to receive a balloon for actuating the at least one expandable support element,
   wherein the side channel is configured to extend outside the disrupted vessel to provide access to the first lumen from outside the disrupted vessel, and the side channel is configured to discourage folding along the first lumen;
   a bifurcation at a portion of the graft defined by an intersection of the first lumen and the second lumen; and
   an elongate aperture in the graft circumscribing the bifurcation and having a closed configuration and an open configuration such that when the aperture is in the closed configuration it defines a clot-resistant inner graft surface, wherein the aperture closes upon itself along a generally straight line in the closed configuration, and when the aperture is in the open configuration it is configured to provide access to the first lumen for a balloon for actuating the at least one expandable support element.

2. The expandable shunt of claim 1, wherein the length of the graft near at least one of the first and second ends of the graft supported by the at least one expandable support element from within the graft is greater than or equal to the maximum expanded-state diameter of the first lumen.

3. The expandable shunt of claim 1, wherein a ratio of the length of the graft near at least one of the first and second ends of the graft supported by the at least one expandable support element from within the graft to the maximum expanded-state diameter of the first lumen is in a range from 1:1 to 2.5:1.

4. The expandable shunt of claim 1, wherein a ratio of the length of the graft near at least one of the first and second ends of the graft supported by the at least one expandable support element from within the graft to the maximum expanded-state diameter of the first lumen is in a range of 1:1 to 3:1.

5. The expandable shunt of claim 1, wherein the at least one expandable support element is configured for engaging the disrupted vessel to secure the graft to the disrupted vessel.

6. The expandable shunt of claim 1, further comprising at least one balloon for actuating the at least one expandable support element, the at least one balloon being placed within the at least one expandable support element from outside the disrupted vessel through the elongate aperture.

7. The expandable shunt of claim 1, further comprising at least one balloon for actuating the at least one expandable support element, the at least one balloon being removable from the graft.

8. A system for treating disrupted vessels, comprising:
at least one graft comprising an aperture and a lumen having a maximum expanded-state diameter and extending between first and second ends of the at least one graft;
at least one expandable support element supporting a length of the at least one graft from within near at least one of the first and second ends of the at least one graft,
wherein the at least one expandable support element is configured for engaging a disrupted vessel to secure the at least one graft to the disrupted vessel;
at least one balloon for actuating the at least one expandable support element, the at least one balloon being removable from the at least one graft;
at least one side channel configured to extend outside the disrupted vessel to provide access of the at least one balloon to the lumen from outside the disrupted vessel through the aperture to align the at least one balloon within the at least one expandable support element,
wherein the at least one side channel is configured to discourage folding along the lumen, and
wherein the aperture having a closed configuration and an open configuration such that when the aperture is in the closed configuration it defines a clot-resistant inner graft surface, wherein the aperture closes upon itself along a generally straight line in the closed configuration, and when the aperture is in the open configuration it is configured to provide access to the lumen for the at least one balloon for actuating the at least one expandable support element.

9. The system of claim 8, wherein the length of the at least one graft near at least one of the first and second ends of the at least one graft supported by the at least one expandable support element from within the at least one graft is greater than or equal to the maximum expanded-state diameter of the lumen.

10. The system of claim 8, wherein a ratio of the length of the at least one graft near at least one of the first and second ends of the at least one graft supported by the at least one expandable support element from within the at least one graft to the maximum expanded-state diameter of the lumen is in a range from 1:1 to 2.5:1.

11. The system of claim 8, wherein a ratio of the length of the at least one graft near at least one of the first and second ends of the at least one graft supported by the at least one expandable support element from within the at least one graft to the maximum expanded-state diameter of the lumen is in a range of 1:1 to 3:1.

12. A balloon expandable shunt for shunting a disrupted vessel, comprising:
a graft defining a first lumen having a maximum expanded-state diameter and extending between first and second ends of the graft;
at least one expandable support element supporting a length of the graft from within near at least one of the first and second ends of the graft,
wherein a ratio of the length of the graft near at least one of the first and second ends of the graft supported by the at least one expandable support element from within the graft to the maximum expanded-state diameter of the first lumen is at least 1:1;
a side channel defining a second lumen and configured to receive a balloon for actuating the at least one expandable support element,
wherein the side channel is configured to extend outside the disrupted vessel to provide access to the first lumen from outside the disrupted vessel, and the side channel is configured to discourage folding along the first lumen;
a bifurcation at a portion of the graft defined by an intersection of the first lumen and the second lumen; and
an elongate aperture in the graft circumscribing the bifurcation and having a closed configuration and an open configuration such that when the aperture is in the closed configuration it defines a clot-resistant inner graft surface, wherein the aperture closes upon itself along a generally straight line in the closed configuration, and when the aperture is in the open configuration it is configured to provide access to the first lumen for a balloon for actuating the at least one expandable support element.

13. The balloon expandable shunt of claim 12, wherein the ratio of the length of the graft near at least one of the first and second ends of the graft supported by the at least one expandable support element from within the graft to the maximum expanded-state diameter of the first lumen is in a range of 1:1 to 2:1.

14. The balloon expandable shunt of claim 12, wherein the ratio of the length of the graft near at least one of the first and second ends of the graft supported by the at least one expandable support element from within the graft to the maximum expanded-state diameter of the first lumen is in a range from 1:1 to 2.5:1.

15. The balloon expandable shunt of claim 12, wherein the ratio of the length of the graft near at least one of the first and second ends of the graft supported by the at least one expandable support element from within the graft to the maximum expanded-state diameter of the first lumen is in a range of 1:1 to 3:1.

16. The balloon expandable shunt of claim 12, wherein the at least one expandable support element is coupled to and extends beyond the graft near at least one of the first and second ends of the graft.

17. The balloon expandable shunt of claim 12, wherein the at least one expandable support element extends through the first lumen between the first and second ends of the graft.

18. The balloon expandable shunt of claim 12, wherein the at least one expandable support element is configured for engaging the disrupted vessel to secure the graft to the disrupted vessel.

19. The balloon expandable shunt of claim 12, wherein the graft comprises a plurality of expandable support elements with at least one support element being disposed to one side of the side channel and another support element being disposed to another side of the side channel, and wherein the side channel is configured for receiving a balloon that extends to both sides of the side channel so as to expand both support elements.

20. The balloon expandable shunt of claim 12, wherein the side channel is configured to receive a medical implement.

21. The balloon expandable shunt of claim 12, further comprising at least one sealing member adapted to seal the side channel.

\* \* \* \* \*